United States Patent
Takada et al.

(10) Patent No.: US 9,603,513 B2
(45) Date of Patent: Mar. 28, 2017

(54) MEDICINAL SOLUTION COLLECTING TOOL AND ENDOSCOPE CLEANING/DISINFECTING APPARATUS

(71) Applicant: OLYMPUS CORPORATION, Tokyo (JP)

(72) Inventors: Hiroo Takada, Tachikawa (JP); Hisato Kogure, Hidaka (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/996,899

(22) Filed: Jan. 15, 2016

(65) Prior Publication Data

US 2016/0128554 A1    May 12, 2016

Related U.S. Application Data

(63) Continuation of application No. PCT/JP2015/055620, filed on Feb. 26, 2015.

(30) Foreign Application Priority Data

Sep. 16, 2014  (JP) ................... 2014-188043

(51) Int. Cl.
   *B08B 9/027* (2006.01)
   *G01N 1/10* (2006.01)
   *A61B 1/12* (2006.01)
   *B01L 3/02* (2006.01)

(52) U.S. Cl.
   CPC ............... *A61B 1/123* (2013.01); *B01L 3/02* (2013.01); *B08B 9/027* (2013.01); *G01N 1/10* (2013.01)

(58) Field of Classification Search
   USPC ....................................... 134/116
   See application file for complete search history.

(56) References Cited

U.S. PATENT DOCUMENTS

| 5,307,696 | A | * | 5/1994 | Allain ............... | G01N 1/10 141/131 |
| 5,337,620 | A | * | 8/1994 | Kalidini ............ | G01N 1/08 73/864.64 |
| 2013/0125934 | A1 | | 5/2013 | Komiya et al. | |

FOREIGN PATENT DOCUMENTS

| EP | 2638847 A1 | | 9/2013 |
| JP | 2011-092425 A | | 5/2011 |
| JP | 2011092425 A | * | 5/2011 |
| JP | 5253682 B1 | | 7/2013 |
| WO | WO 2013/011724 A1 | | 1/2013 |

* cited by examiner

*Primary Examiner* — Michael Barr
*Assistant Examiner* — Cristi Tate-Sims
(74) *Attorney, Agent, or Firm* — Scully, Scott, Murphy & Presser, PC

(57) ABSTRACT

A medicinal solution collecting tool of the invention includes: a pillar-shaped portion including an insertion end and a withdrawal end; a collecting section provided on the insertion end side of the pillar-shaped portion; a collecting port provided on a surface of the pillar-shaped portion; and a guide section provided on the surface of the pillar-shaped portion, the guide section including a first guide section being convex or concave and parallel to an axial direction of the pillar-shaped portion, and a second guide section provided on the withdrawal end side relative to the first guide section, the second guide section being convex or concave and crossing the axial direction of the pillar-shaped portion.

4 Claims, 14 Drawing Sheets

$\theta = \alpha \, [\text{deg}]$

MEDICINAL SOLUTION COLLECTING TOOL AND ENDOSCOPE CLEANING/DISINFECTING APPARATUS

CROSS REFERENCE TO RELATED APPLICATION

This application is a continuation application of PCT/JP2015/055620 filed on Feb. 26, 2015 and claims benefit of Japanese Application No. 2014-188043 filed in Japan on Sep. 16, 2014, the entire contents of which are incorporated herein by this reference.

BACKGROUND OF THE INVENTION

1. Field of the Invention

The present invention relates to a medicinal solution collecting tool for collecting a medicinal solution stored in a medicinal solution storing section and an endoscope cleaning/disinfecting apparatus which includes the medicinal solution collecting tool.

2. Description of the Related Art

For an endoscope used in a medical field, a reprocessing process using a medicinal solution, such as a disinfection process, is performed after the endoscope is used. As an apparatus which automatically performs a disinfection process using a medicinal solution and the like for an endoscope, for example, an endoscope reprocessing apparatus as disclosed in Japanese Patent Application Laid-Open Publication No. 2011-92425 is known. The endoscope reprocessing apparatus is provided with a medicinal solution storing section which is a container for storing the medicinal solution, in the apparatus.

In a case of performing the reprocessing process using a medicinal solution for an endoscope by the endoscope reprocessing apparatus, a test for confirming whether or not the medicinal solution stored in the medicinal solution storing section has a predetermined processing capability is conducted in advance. The medicinal solution test is, for example, a test for measuring a concentration of the medicinal solution. A predetermined amount of the medicinal solution is collected from the medicinal solution storing section, and the medicinal solution test is conducted for the collected medicinal solution. The work of collecting the medicinal solution for the test from the medicinal solution storing section is performed, for example, by a method of transferring the medicinal solution from a stop-cock provided on the medicinal solution storing section to a beaker or the like.

SUMMARY OF THE INVENTION

A medicinal solution collecting tool according to an aspect of the present invention is a medicinal solution collecting tool to be inserted into a medical solution storing section for endoscope reprocessing to collect a medicinal solution from an inside of the medicinal solution storing section, the medicinal solution collecting tool including: a pillar-shaped portion including an insertion end and a withdrawal end; a collecting section provided on the insertion end side of the pillar-shaped portion, the collecting section being a cavity for collecting the medicinal solution; a collecting port which is an opening provided on a surface of the pillar-shaped portion, the collecting port communicating with the collecting section; and a guide section provided on the surface of the pillar-shaped portion, the guide section including a first guide section being convex or concave and parallel to an axial direction of the pillar-shaped portion, and a second guide section provided on the withdrawal end side relative to the first guide section on the surface of the pillar-shaped portion, the second guide section being convex or concave and crossing the axial direction of the pillar-shaped portion.

Further, an endoscope cleaning/disinfecting apparatus according to an aspect of the present invention includes: the medicinal solution collecting tool; and a medicinal solution storing section storing a medicinal solution, the medicinal solution storing section including an introduction port for introducing the medicinal solution collecting tool.

DETAILED DESCRIPTION OF THE PREFERRED EMBODIMENTS

Preferred embodiments of the present invention will be described below with reference to drawings. Note that, in each figure used in description below, a different reduced scale is used for each component so that each component is shown in a size recognizable on a drawing, and the present invention is not limited only to the number of components, shapes of the components, a ratio of sizes of the components and relative positional relationships among the respective components shown in the figures.

An example of the embodiments of the present invention will be described below. A medicinal solution collecting tool 1 is a device for collecting, from an inside of a medicinal solution storing section 30 which stores a medicinal solution for endoscope reprocessing, a part of the medicinal solution. A purpose and kind of the medicinal solution is not especially limited. In the present embodiment, the medicinal solution is a peracetic acid solution for performing a disinfection process for an endoscope as an example.

Figure 1:
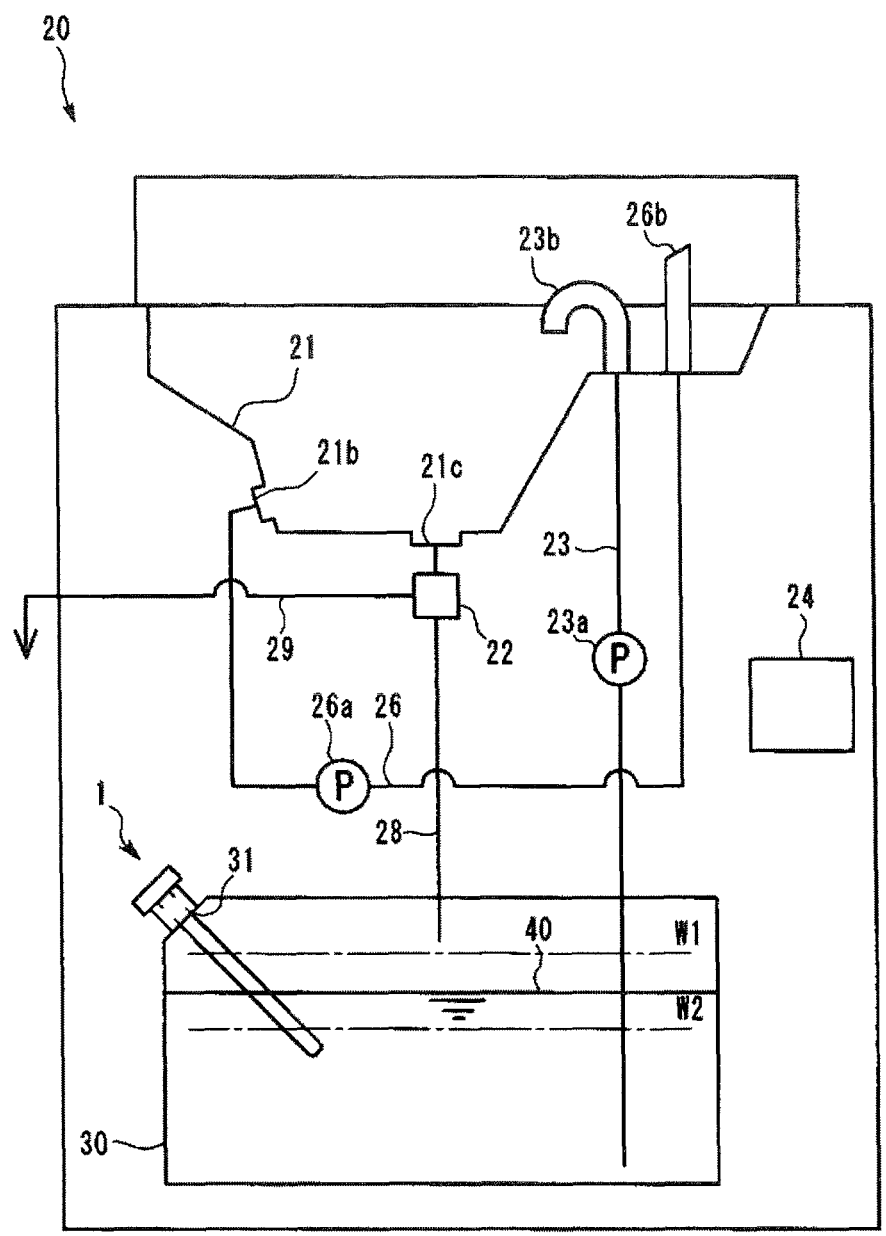
FIG. 1 is a diagram showing a schematic configuration of an endoscope cleaning/disinfecting apparatus of a first embodiment.

The medicinal solution storing section 30 only has to be a device having a container-shaped configuration and internally storing the medicinal solution. For example, the medicinal solution storing section 30 may be in a form of existing as a single item, for example, like a bottle or a can, or may be in a form of being connected to or included in another device. In the present embodiment, as an example, the medicinal solution storing section 30 is a container arranged in an endoscope cleaning/disinfecting apparatus 20 and storing a medicinal solution 40 as shown in FIG. 1.

The endoscope cleaning/disinfecting apparatus 20 is an apparatus which performs a rinsing process, a cleaning process and a disinfection process for at least one of an endoscope and endoscopic accessories (neither of them are shown) using water or a medicinal solution such as cleaning liquid and disinfection liquid.

The endoscope cleaning/disinfecting apparatus 20 is configured, including a control section 24, a processing tank 21 and the medicinal solution storing section 30. The processing tank 21 is in a recess shape having an opening portion which opens upward, and at least one of an endoscope and endoscopic accessories can be arranged inside. The processing tank 21 is configured being capable of storing liquid inside.

The control section 24 is a device which controls an operation of each component of the endoscope cleaning/disinfecting apparatus 20 on a basis of a predetermined program, and the control section 24 is configured with a computer configured, having, for example, an arithmetic unit, a storage device, an auxiliary storage device and an input/output device.

A medicinal solution injection nozzle 23b, a circulation nozzle 26b, a circulation port 21b and a liquid discharge port 21c are provided in the processing tank 21.

The medicinal solution injection nozzle 23b is connected to the medicinal solution storing section 30 via a medicinal solution injection conduit 23. A medicinal solution injection pump 23a is arranged on the medicinal solution injection conduit 23. By an operation of the medicinal solution injection pump 23a, the medicinal solution 40 stored in the medicinal solution storing section 30 is sent into the processing tank 21 through the medicinal solution injection conduit 23 and the medicinal solution injection nozzle 23b.

The circulation nozzle 26b and the circulation port 21b are opening portions which open to the inside of the processing tank 21, and they communicate with each other via a circulation conduit 26. A circulation pump 26a is arranged on the circulation conduit 26. By an operation of the circulation pump 26a, the liquid in the processing tank 21 is sucked out from the circulation port 21b and then returns into the processing tank 21 via the circulation conduit 26 and the circulation nozzle 26b. By arranging at least one of an endoscope and endoscopic accessories in the processing tank 21, injecting the medicinal solution 40, which is disinfection liquid, into the processing tank 21 and then circulating the medicinal solution 40, the endoscope cleaning/disinfecting apparatus 20 performs a disinfection process and the like for at least one of the endoscope and the endoscopic accessories.

The liquid discharge port 21c is a part which discharges the liquid in the processing tank 21. The liquid discharge port 21c is connected to a recovery conduit 28 and a discharge conduit 29 via a switching valve 22. The switching valve 22 can switch between a state in which the liquid discharge port 21c is open and is connected to either the recovery conduit 28 or the discharge conduit 29 and a state in which the liquid discharge port 21c is closed.

The recovery conduit 28 connects the switching valve 22 and the medicinal solution storing section 30 to each other. If, in a state in which the medicinal solution 40 is stored in the processing tank 21, the liquid discharge port 21c is opened, and the liquid discharge port 21c and the discharge conduit 29 are connected to each other, the medicinal solution 40 in the processing tank 21 is recovered into the medicinal solution storing section 30.

The discharge conduit 29 extends, for example, to an outside of the endoscope cleaning/disinfecting apparatus 20. If the liquid discharge port 21c is opened, and the liquid discharge port 21c and the discharge conduit 29 are connected to each other, the liquid stored in the processing tank 21 is discharged to the outside of the endoscope cleaning/disinfecting apparatus 20.

Note that, though the endoscope cleaning/disinfecting apparatus 20 is provided with a configuration for storing a cleaning agent and injecting the cleaning agent into the processing tank 21, a configuration for sending alcohol, tap water or air into the processing tank 21, and the like, in addition to the configuration described before, the configurations are similar to those of an already-known endoscope cleaning/disinfecting apparatus, and, therefore, description thereof will be omitted.

The medicinal solution storing section 30 is a container-shaped member which internally stores the medicinal solution 40 which is liquid. As described before, the medicinal solution injection conduit 23 and the recovery conduit 28 are connected to the medicinal solution storing section 30 to make it possible to cause the medicinal solution 40 to come and go between the medicinal solution storing section 30 and the processing tank 21.

The medicinal solution storing section 30 is provided with a configuration for replacing the medicinal solution 40 which the medicinal solution storing section 30 internally stores, though it is not shown. More specifically, a discharge port for discharging old medicinal solution 40 in the medicinal solution storing section 30 to an outside of the medicinal solution storing section 30 and an injection port for injecting new medicinal solution 40 into the medicinal solution storing section 30 are arranged on the medicinal solution storing section 30.

Figure 2:
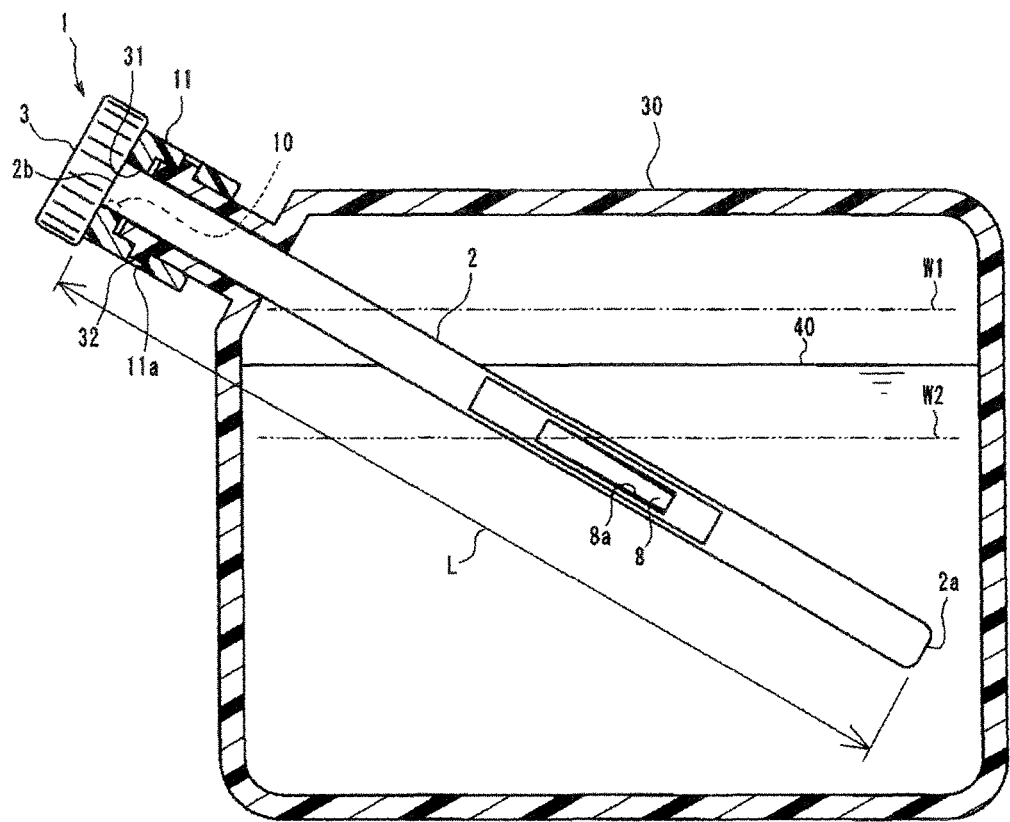
FIG. 2 is a diagram showing a state in which a medicinal solution collecting tool of the first embodiment is located at a first position in an introduction port.

As shown in FIG. 2, the medicinal solution storing section 30 is provided with an introduction port 31, which is an opening portion for introducing a medicinal solution collecting tool 1 to be described later, from the outside of the medicinal solution storing section 30 into the medicinal solution storing section 30. The introduction port 31 is provided at a position upper than a highest water level W1 of the medicinal solution storing section 30. The highest water level W1 is a highest position which a liquid surface of the medicinal solution 40 can reach in the medicinal solution storing section 30. Note that a water gauge may be provided in the medical solution storing section 30 so that the liquid surface of the medicinal solution 40 does not exceed the highest water level W1, though it is not shown.

The introduction port 31 is provided with a follower 10. The follower 10 is a part to engage with a guide section 4 (not shown in FIG. 2) of the medicinal solution collecting tool 1 to be described later.

Figure 7:
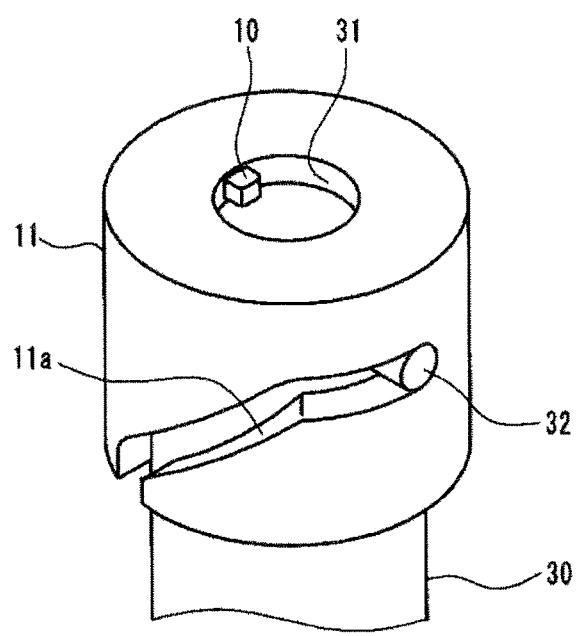
FIG. 7 is a perspective view enlargingly showing the introduction port of a medicinal solution storing section.

The follower 10 is a part which has a shape corresponding to a form of the guide section 4 of the medicinal solution collecting tool 1, and the shape is not especially limited. In the present embodiment, as an example, the follower 10 is a projecting portion in a protrusion shape which projects inward in a radial direction, from an inner circumferential surface of the introduction port 31 as shown in FIG. 7. The guide section 4 of the medicinal solution collecting tool 1 is a concave groove portion which is provided on a surface of the medicinal solution collecting tool 1, and the follower 10 fits in the concave guide section 4 in a slidable state.

Further, in the present embodiment, as an example, the follower 10 is configured such that it can be removed from the medicinal solution storing section 30. More specifically, the follower 10 is provided on a ring-shaped member 11 which is removably fixed at an end portion of the introduction port 31.

Figure 8:
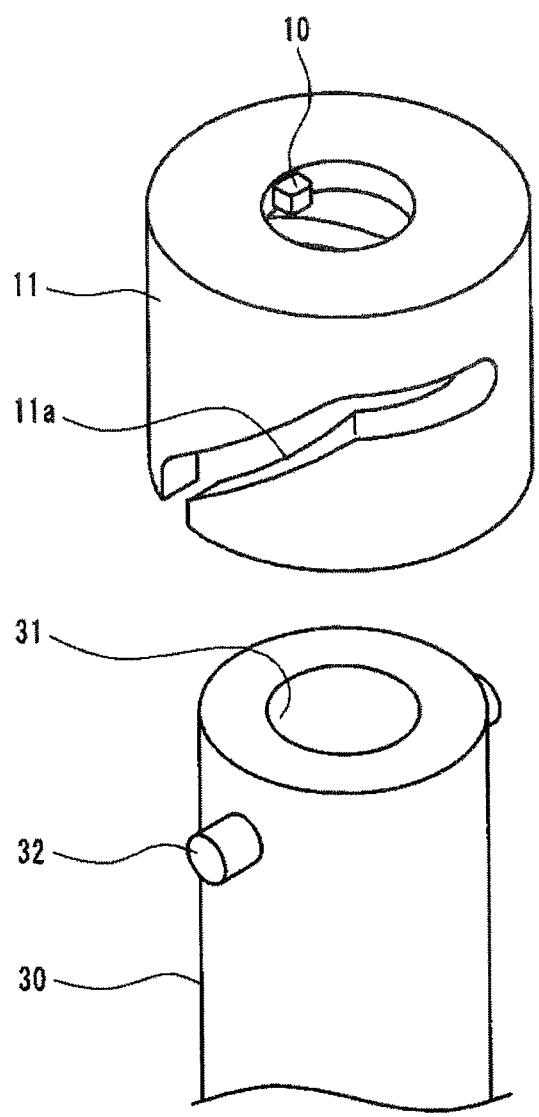
FIG. 8 is a perspective view showing a state in which a follower is removed from the medicinal solution storing section.

As shown in FIGS. 7 and 8, the end portion of the introduction port 31 is in a cylindrical shape, and the ring-shaped member 11 fits to an outer circumference of the end portion of the cylinder-shaped introduction port 31. Further, a convex boss 32 projecting outward in a radial direction is formed on the end portion of the introduction port 31. A notch portion 11a which engages with the boss 32 is formed on the ring-shaped member 11. By causing the boss 32 and the notch portion 11a to engage with each other, the ring-shaped member 11 and the follower 10 are fixed at predetermined positions on the introduction port 31. Note that the configuration of fixing the ring-shaped member 11 on the introduction port 31 is not limited to the shown present embodiment, and, for example, a form of the ring-shaped member 11 being fixed on the introduction port 31 by screw fastening or a form of the ring-shaped member 11 being fixed on the introduction port 31 by adhesive are also possible.

By causing the follower 10 to be removable from the medicinal solution storing section 30 as in the present embodiment, it is possible to, for example, in a case of abrasion or fracture of the follower 10, perform work of replacing the follower 10 easily. Note that the follower 10 may be formed integrally with the medicinal solution storing section 30.

Figure 3:
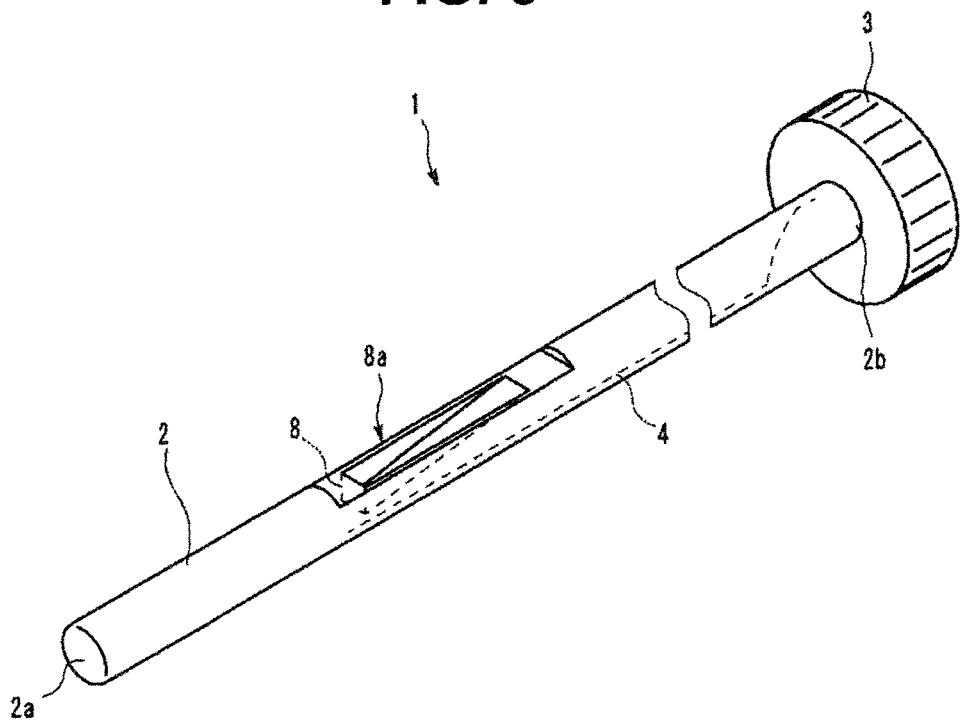
FIG. 3 is a perspective view showing a plane on which a collecting port of the medicinal solution collecting tool of the first embodiment is provided.

Next, a configuration of the medicinal solution collecting tool 1 will be described. The medicinal solution collecting tool 1 is provided with a rod-shaped pillar-shaped portion 2 which can be inserted into the introduction port 31 as shown in FIGS. 2 and 3.

Though, in the present embodiment, the pillar-shaped portion 2 is in a cylindrical shape which is linear in a longitudinal direction as an example, another shapes, for example, an elliptic cylinder, a quadrangular prism, an octogonal prism or a combination of these is also possible. Further, it is also possible to cause a shape of a part where the guide section is arranged to be different from shapes of other parts. For example, it is preferable that at least the part where the guide section is arranged is in a cylindrical shape.

A direction along a central axis parallel to the longitudinal direction of the pillar-shaped portion 2 which is in a rod shape will be referred to as an axial direction below. Further, a movement of the pillar-shaped portion 2 inserted in the introduction port 31 in a direction of advancing into the medicinal solution storing section 30 will be referred to as an insertion-direction movement, and a movement of the pillar-shaped portion 2 inserted in the introduction port 31 in a direction of withdrawing out of the medicinal solution storing section 30 will be referred to as a withdrawal-direction movement.

An outer diameter of the pillar-shaped portion 2 is shorter than an inner diameter of the introduction port 31. Further, the outer diameter of the pillar-shaped portion 2 is determined so that the guide section 4 provided on an outer circumferential surface of the pillar-shaped portion 2 and the follower 10 provided on the inner circumferential surface of the introduction port 31 continuously engage with each other in a state in which the pillar-shaped portion 2 is inserted in the introduction port 31. The follower 10 of the present embodiment is in a protrusion shape projecting from the inner circumferential surface of the introduction port 31, and the outer diameter of the pillar-shaped portion 2 is determined so that the follower 10 does not fall off out of the concave guide section 4.

A direction in which the pillar-shaped portion 2 is to be inserted into the introduction port 31 is specified. An end portion of the pillar-shaped portion 2 which projects into the medicinal solution storing section 30 in the state in which the pillar-shaped portion 2 is inserted in the introduction port 31 (the state in FIG. 2) will be referred to as an insertion end 2a, and an opposite end portion will be referred to as a withdrawal end 2b below. That is, the pillar-shaped portion 2 is inserted into the introduction port 31 so that the insertion end 2a side projects into the medicinal solution storing section 30.

In the state in which the pillar-shaped portion 2 is inserted in the introduction port 31, the central axis of the pillar-shaped portion 2 which is parallel to the longitudinal direction inclines with a predetermined angle relative to a vertical axis, and the insertion end 2a is located lower than the withdrawal end 2b. That is, in a case of causing the pillar-shaped portion 2 to move in an insertion direction, the pillar-shaped portion 2 advances obliquely downward.

A length for which the pillar-shaped portion 2 can move in the insertion direction in the introduction port 31 is specified. More specifically, the pillar-shaped portion 2 can be inserted into the introduction port 31 by a predetermined length L from the insertion end 2a toward the withdrawal end 2b as shown in FIG. 2. That is, if the pillar-shaped portion 2 is located at an end of a movable range in the insertion direction in the introduction port 31, the pillar-shaped portion 2 has advanced into the introduction port 31 by the predetermined length L from the insertion end 2a.

A position of the pillar-shaped portion 2 in the state in which the pillar-shaped portion 2 is inserted in the introduction port 31 by the length L will be referred to as a first position P1 below. That is, a state in which the pillar-shaped portion 2 exists at the first position P1 is a state in which the pillar-shaped portion 2 has advanced to deepest in the medicinal solution storing section 30 from the introduction port 31.

A configuration for specifying the length L by which the pillar-shaped portion 2 can be inserted in the introduction port 31 is not especially limited. In the present embodiment, as an example, a length from the insertion end 2a of the pillar-shaped portion 2 to the withdrawal end 2b is L, and a handle section 3 having an outer diameter larger than the inner diameter of the introduction port 31 is provided at the withdrawal end 2b of the pillar-shaped portion 2. In a state in which the whole pillar-shaped portion 2 with the length L is inserted in the introduction port 31, the handle section 3 comes into contact with an opening end of the introduction port 31, and further movement of the pillar-shaped portion 2 in the insertion direction is restricted (the state shown in FIG. 2).

As described before, in the state of being inserted in the introduction port 31, the pillar-shaped portion 2 is in such an attitude that the central axis inclines so that the insertion end 2a is located lower than the withdrawal end 2b. Therefore, a force of movement in the insertion direction is continuously applied to the pillar-shaped portion 2 by gravity. Therefore, if the pillar-shaped portion 2 is inserted in the introduction port 31, and an external force is not applied, the medicinal solution collecting tool 1 moves to the first position P1 by its own weight.

When the pillar-shaped portion 2 is located at the first position P1 as shown in FIG. 2, the insertion end 2a of the pillar-shaped portion 2 is located lower than a lowest water level W2 of the medicinal solution storing section 30. Here, the lowest water level W2 is a height of the liquid surface in a case where a smallest volume of medicinal solution 40 that enables execution of a process using the medicinal solution 40 by the endoscope cleaning/disinfecting apparatus 20 is stored in the medicinal solution storing section 30. Therefore, if the endoscope cleaning/disinfecting apparatus 20 is in a stop state of the endoscope cleaning/disinfecting apparatus 20 or in a state of not executing the process using the medicinal solution 40, the liquid surface of the medicinal solution 40 in the medicinal solution storing section 30 is located upper than the lowest water level W2. Therefore, when the endoscope cleaning/disinfecting apparatus 20 is in the stop state or in the state of not executing the process using the medicinal solution 40, and the pillar-shaped portion 2 is at the first position P1, the insertion end 2a of the pillar-shaped portion 2 sinks under the medicinal solution 40.

Figure 6:
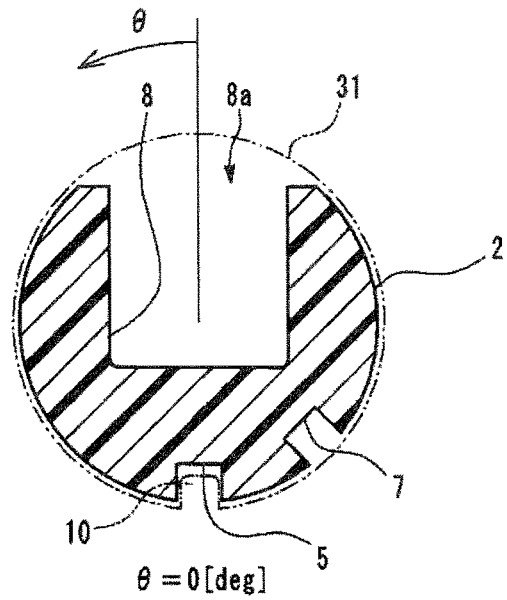
FIG. 6 is a diagram of a VI-VI cross section in FIG. 5.

The pillar-shaped portion 2 is provided with a collecting section 8. As shown in FIGS. 3 and 6, the collecting section 8 is a cavity portion formed in the pillar-shaped portion 2. Further, a collecting port 8a, which is an opening communicating with the collecting section 8, is provided on the surface of the pillar-shaped portion 2. If the collecting port 8a is in a state of facing upward, the collecting section 8 can internally store liquid.

Further, the pillar-shaped portion 2 is provided with the guide section 4. The guide section 4 is a convex or concave part to be engaged with the follower 10 fixed on the introduction port 31 described before. In the present embodiment, as an example, the guide section 4 is in a form of a concave cam groove because the follower 10 is in a protrusion shape.

Figure 4:
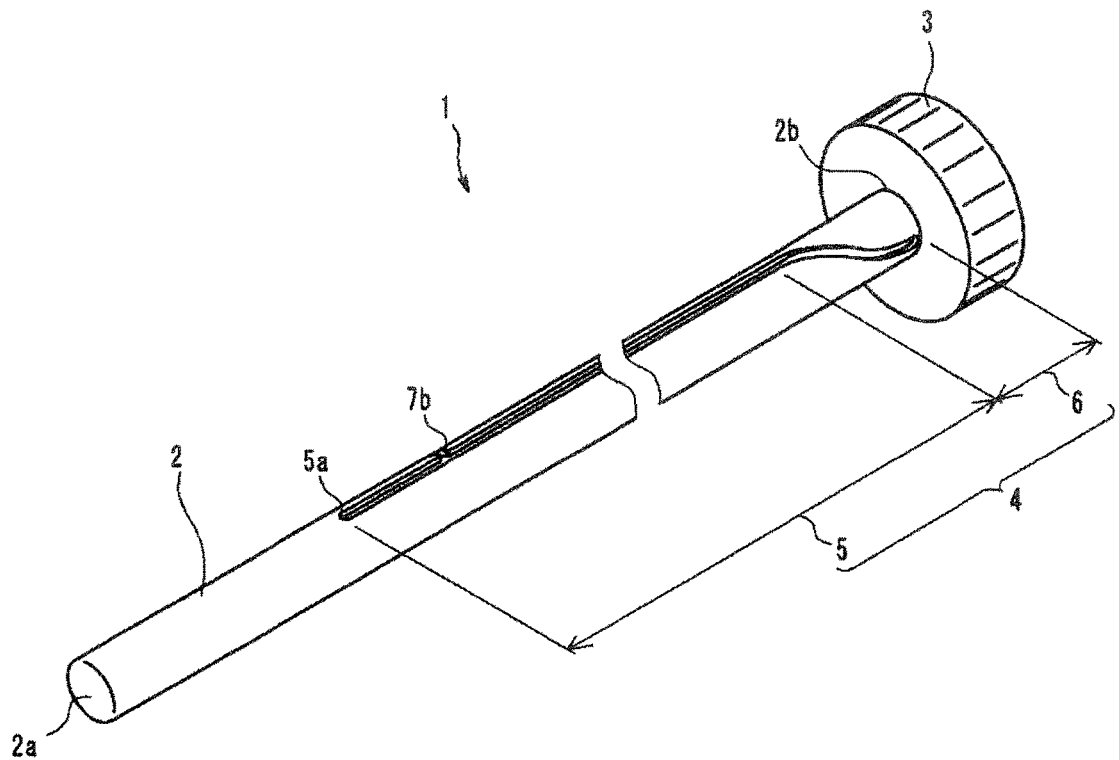
FIG. 4 is a perspective view showing a plane on which a guide section of the medicinal solution collecting tool of the first embodiment is provided.
Figure 5:
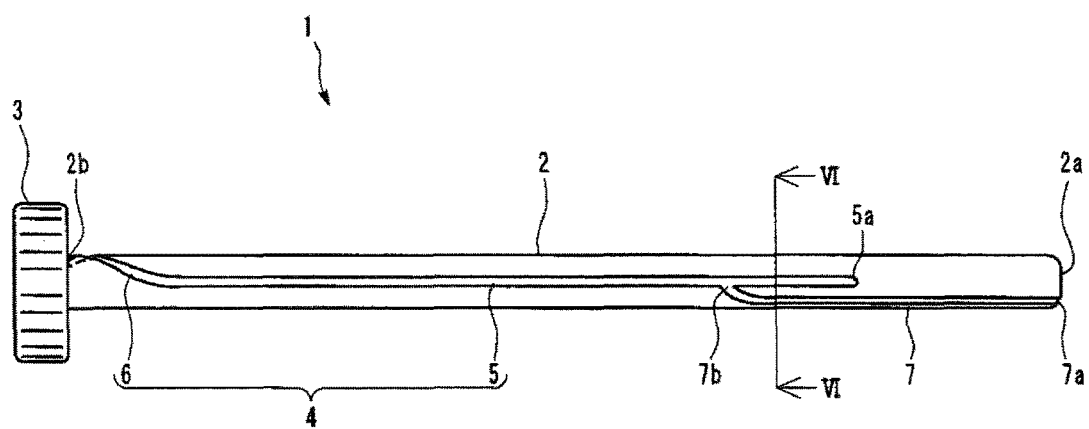
FIG. 5 is a diagram of the guide section of the medicinal solution collecting tool of the first embodiment seen from a front.

As shown in FIGS. 4 and 5, the guide section 4 is a groove-shaped part formed at a position on the surface of the pillar-shaped portion 2 which does not overlap with the collecting port 8a. The convex follower 10 can slide along the guide section 4 in a state of fitting in the groove-shaped guide section 4.

The guide section 4 includes a first guide section 5, which is a section on the insertion end 2a side of the pillar-shaped portion 2 and a second guide section 6, which is a section on the withdrawal end 2b side relative to the first guide section 5. The first guide section 5 and the second guide section 6 are connected to each other, and the follower 10 can come and go between the first guide section 5 and the second guide section 6 while maintaining a state of engaging with the first guide section 5 and the second guide section 6. That is, the follower 10 becomes engaging with the first guide section 5 or the second guide section 6 according to an axial direction position of the pillar-shaped portion 2.

However, if the first guide section 5 and the second guide section 6 are convex, the first guide section 5 and the second guide section 6 may be away from each other by such a distance that the neither first guide section 5 nor the second guide section 6 falls off from the follower 10.

If the pillar-shaped portion 2 is located between the first position P1 (the state shown in FIG. 2) and a second position P2 away from the first position P1 by a predetermined distance L2 in the withdrawal direction (a state shown in FIG. 9), the follower 10 engages with the second guide section 6. That is, if the pillar-shaped portion 2 is located on an insertion side relative to the second position P2, the follower 10 engages with the second guide section 6. If the pillar-shaped portion 2 is located on a withdrawal side relative to the second position P2, the follower 10 engages with the first guide section 5.

In a state in which the pillar-shaped portion 2 is located at the second position P2, and when the pillar-shaped portion 2 is located on the insertion side relative to the second position P2, the collecting port 8a and the collecting section 8 provided on the pillar-shaped portion 2 are located lower than the lowest water level W2 of the medicinal solution storing section 30.

The first guide section 5 is a linear groove extending parallel to the axial direction of the pillar-shaped portion 2. Since the first guide section 5 is parallel to the axial direction, the pillar-shaped portion 2 can move forward and backward in the axial direction, and rotation around an axis is restricted, in the state in which the follower 10 engages with the first guide section 5. Here, as for an attitude of the pillar-shaped portion 2 around the axis in the state in which the follower 10 engages with the first guide section 5, the attitude is maintained at an angle which causes the collecting port 8a to face vertically upward.

That is, the first guide section 5 is a part which, when the pillar-shaped portion 2 is located on the withdrawal side relative to the second position P2, guides the pillar-shaped portion 2 to move in the axial direction while maintaining the attitude of the pillar-shaped portion 2 around the axis, at the angle which causes the collecting port 8a to face vertically upward.

Figure 10:
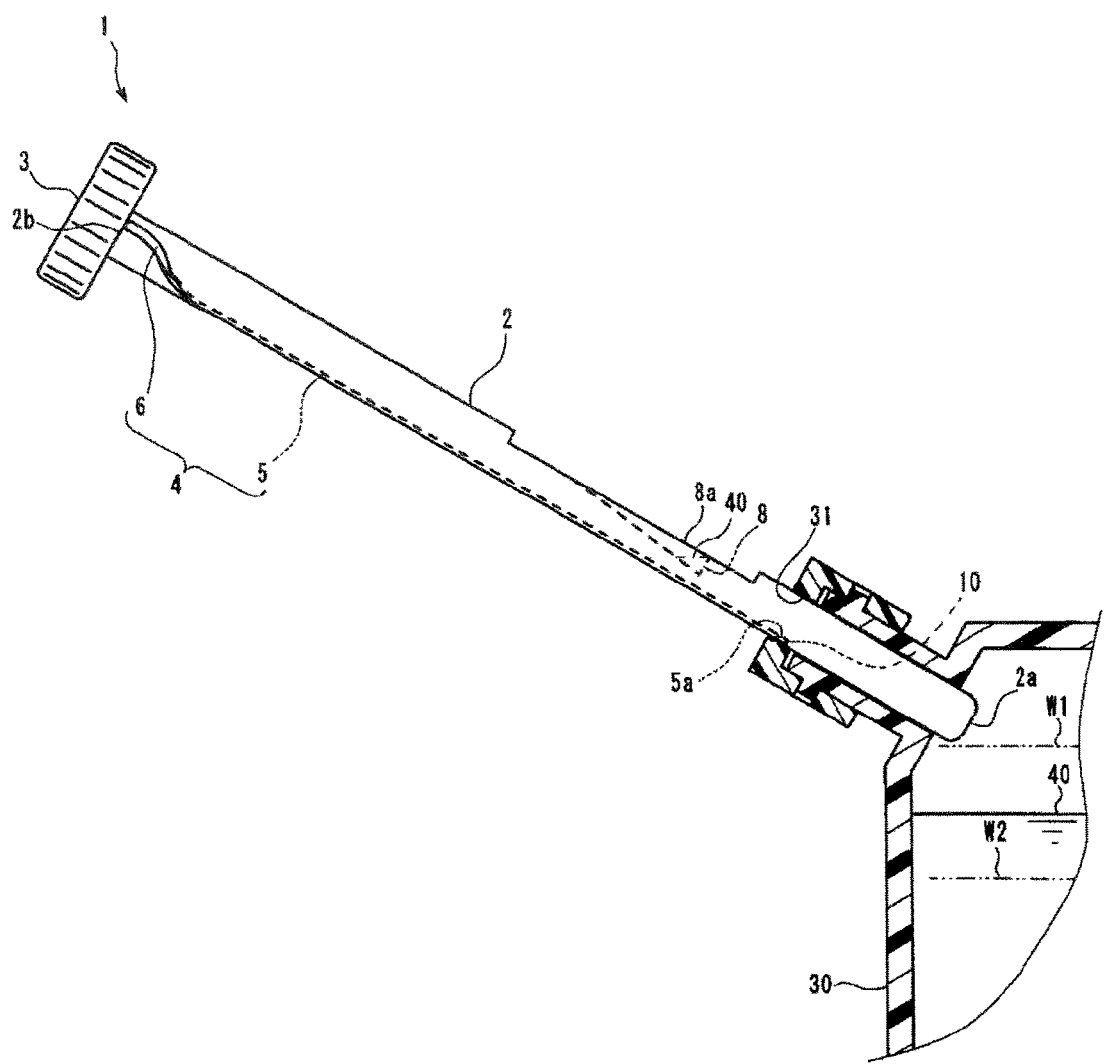
FIG. 10 is a diagram showing a state in which the medicinal solution collecting tool of the first embodiment is located at a third position in the introduction port.

Further, in the present embodiment, as an example, the first guide section 5 defines an end of a range within which the pillar-shaped portion 2 can move in the withdrawal direction in the introduction port 31. More specifically, as shown in FIGS. 4 and 5, an end portion 5a on the insertion end 2*a* side of the first guide section 5 is closed, and, by the follower 10 abutting the end portion 5*a*, further movement of the pillar-shaped portion 2 in the withdrawal direction is restricted (a state in FIG. 10). Thereby, the pillar-shaped portion 2 is prevented from falling off out of the introduction port 31 in the withdrawal direction.

A position of the pillar-shaped portion 2 in the state in which the follower 10 abuts the end portion 5*a* on the insertion end 2*a* side of the first guide section 5 will be referred to as a third position P3. That is, the third position P3 is a state in which the pillar-shaped portion 2 is withdrawn most out of the introduction port 31 in the withdrawal direction.

When the pillar-shaped portion 2 is located at the third position P3, the collecting port 8*a* and the collecting section 8 are located outside the introduction port 31. Further, at this time, since the follower 10 engages with the first guide section 5, the collecting port 8*a* faces vertically upward as described before.

An attachment/detachment guide section 7, which is a groove-shaped part branching from the first guide section 5, is connected at a position on the withdrawal end 2*b* side of the end portion 5*a* on the insertion end 2*a* side of the first guide section 5, at a predetermined distance from the end portion 5*a*. The attachment/detachment guide section 7 is connected to the first guide section 5 at an end portion 7*b* on the withdrawal end 2*b* side, and an end portion 7*a* on the insertion end 2*a* side is in a state of being open at the insertion end 2*a* of the pillar-shaped portion 2. The attachment/detachment guide section 7 extends in a circumferential direction from a portion of connection with the first guide section 5.

In a case of inserting the pillar-shaped portion 2 from an outside of the introduction port 31 into the introduction port 31, the follower 10 is fitted into the attachment/detachment guide section 7 from the end portion 7*a* on the insertion end 2*a* side of the attachment/detachment guide section 7, and, after that, the follower 10 is caused to reach the first guide section 5 via the attachment/detachment guide section 7. Further, in a case of removing the pillar-shaped portion 2 which is in the state of being inserted in the introduction port 31, out of the introduction port 31, the follower 10 is caused to move to the attachment/detachment guide section 7 by rotating the pillar-shaped portion 2 around the axis after causing the follower 10 to move to a branching portion between the first guide section 5 and the attachment/detachment guide section 7, and the follower 10 is caused to fall off from the end portion 7*a* on the insertion end 2*a* side of the attachment/detachment guide section 7.

The second guide section 6 is connected to an end portion 5*b* on the withdrawal end 2*b* side of the first guide section 5, and it is a groove extending such that it crosses relative to the axial direction of the pillar-shaped portion 2 at a predetermined angle. Since the second guide section 6 extends such that it crosses relative to the axial direction of the pillar-shaped portion 2 at the predetermined angle, it has a spiral shape as shown in FIGS. 4 and 5.

Therefore, if the pillar-shaped portion 2 moves in the axial direction relative to the introduction port 31 in the state in which the follower 10 fixed on the introduction port 31 engages with the second guide section 6, the pillar-shaped portion 2 rotates around the axis. That is, the second guide section 6 is a part which, when the pillar-shaped portion 2 is located between the second position P2 and the first position P1, guides the pillar-shaped portion 2 to move in the axial direction while causing the pillar-shaped portion 2 to rotate around the axis.

When the pillar-shaped portion 2 is located at the first position P1, the second guide section 6 holds the pillar-shaped portion 2 at a position where the pillar-shaped portion 2 has rotated around the axis by a predetermined angle α from the angle which causes the collecting port 8*a* to face vertically upward.

As described before, in the state in which the pillar-shaped portion 2 is located at the second position P2, the attitude of the pillar-shaped portion 2 around the axis is at the angle which causes the collecting port 8*a* to face vertically upward. Here, when a rotation-around-axis angle of the pillar-shaped portion 2 is indicated by θ, and a case where the pillar-shaped portion 2 is located at the second position P2 (a state in FIG. 6) is indicated by θ=0[°], a value of the angle θ becomes larger as the pillar-shaped portion 2 moves in the insertion direction from the second position P2. Then, the pillar-shaped portion 2 advances the deepest in the medicinal solution storing section 30 and located at the first position P1, the angle θ shows a maximum value α (a state in FIG. 11).

Figure 12:
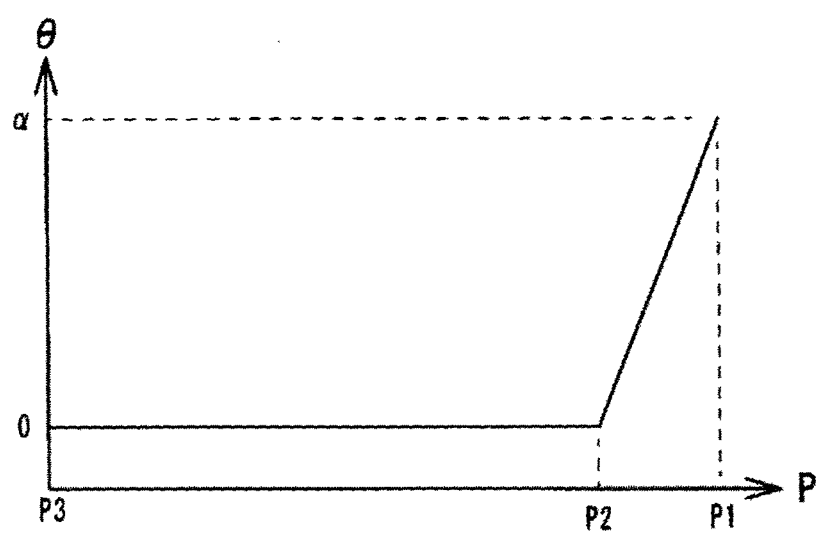
FIG. 12 is a diagram showing a relationship between an axial-direction position of the medicinal solution collecting tool in the introduction port and a rotation-around-axis angle in the first embodiment.

FIG. 12 is a graph showing a relationship between a position P in the introduction port 31 and the rotation-around-axis angle θ of the pillar-shaped portion 2. In FIG. 12, a horizontal axis indicates the position P of the pillar-shaped portion 2 in the introduction port 31, and a vertical axis indicates the rotation-around-axis angle θ of the pillar-shaped portion 2.

Here, the angle α of the pillar-shaped portion 2 in the case where the pillar-shaped portion 2 is located at the first position P1 is an angle at which all the liquid in the collecting section 8 provided on the pillar-shaped portion 2 passes through the collecting port 8*a* and falls outside the pillar-shaped portion 2 by gravity.

Figure 11:
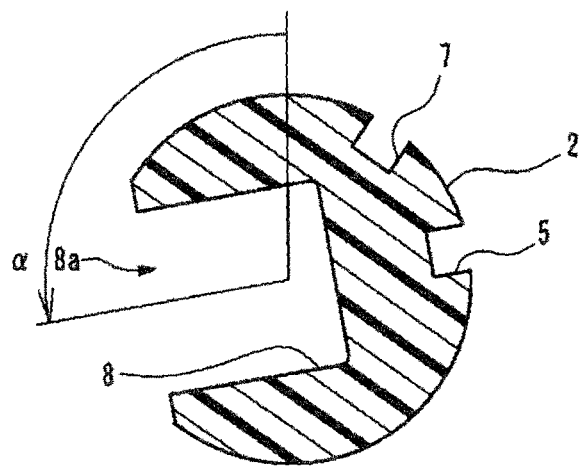
FIG. 11 is a cross-sectional view of a pillar-shaped portion in the state in which the medicinal solution collecting tool of the first embodiment is located at the first position in the introduction port.

For example, if the collecting section 8 is in a recess shape having side walls parallel to each other, on a cross-section by a plane crossing the central axis at right angle, as in the present embodiment shown in FIGS. 6 and 11, the angle α is caused to be a value larger than 90 degrees. Note that, for example, if the collecting section 8 is in a tapered recess shape in which a distance between the side walls becomes shorter as a bottom is nearer, the angle α can be a value smaller than 90 degrees.

An operation of the medicinal solution collecting tool 1 of the present embodiment will be described below. As shown in FIG. 2, when the pillar-shaped portion 2 is located at the end in the insertion direction in the movable range in the introduction port 31 (the first position P1), the collecting port 8*a* and the collecting section 8 are located lower than the lowest water level W2 of the medicinal solution storing section 30. Further, at this time, the attitude of the pillar-shaped portion 2 around the axis is kept at an angle at which the liquid in the collecting section 8 falls outside (θ=α) by engagement between the second guide section 6 and the follower 10.

Figure 9:
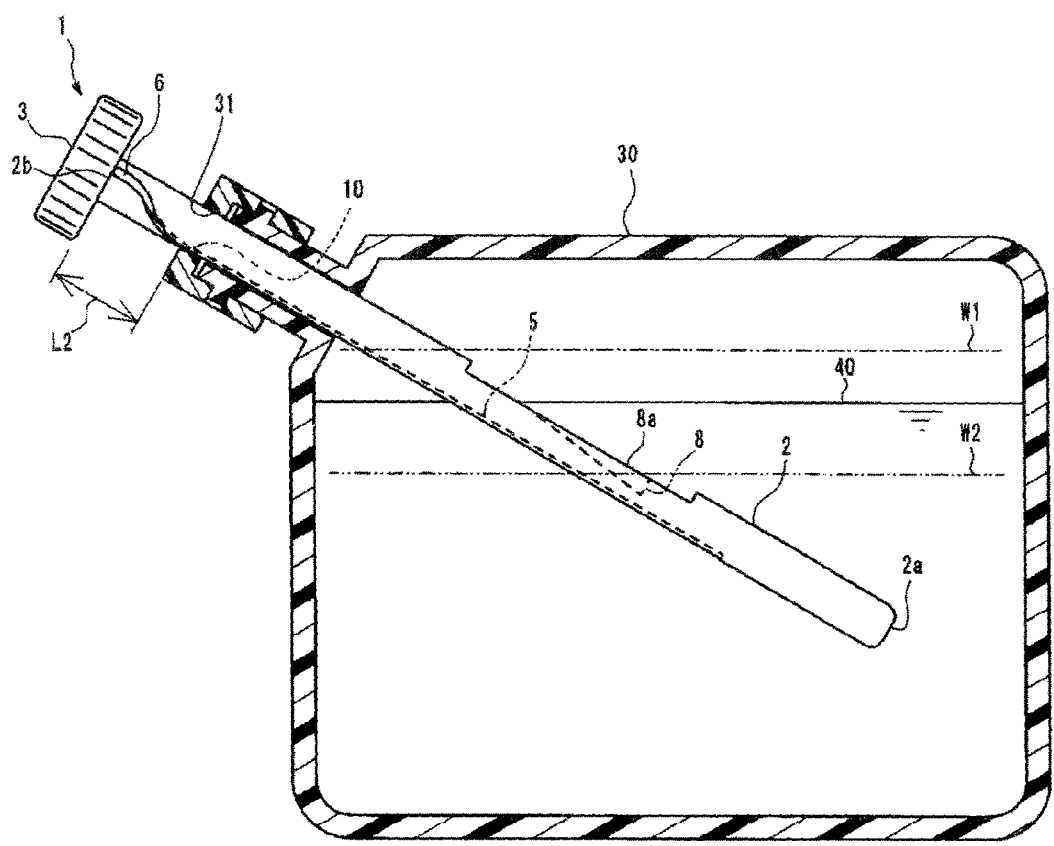
FIG. 9 is a diagram showing a state in which the medicinal solution collecting tool of the first embodiment is located at a second position in the introduction port.

Then, when the pillar-shaped portion 2 moves in the withdrawal direction from the first position P1, for example, by a user grasping and pulling the handle section 3, the attitude of the pillar-shaped portion 2 around the axis is at the angle which causes the collecting port 8*a* to face vertically upward (θ=0) at a time point when the pillar-shaped portion 2 reaches the second position P2 as shown in FIG. 9. At this time, the collecting port 8*a* is located lower than the lowest water level W2 of the medicinal solution storing section 30 and sinks under the medicinal solution 40. Therefore, the collecting section 8 is filled with the medicinal solution 40.

Then, when the pillar-shaped portion 2 moves in the withdrawal direction from the second position P2 to the third position P3, the attitude of the pillar-shaped portion 2 around the axis is continuously kept at the angle which causes the collecting port 8a to face vertically upward (θ=0) by engagement between the first guide section 5 and the follower 10. Therefore, the medicinal solution 40 does not fall from the collecting section 8 and remains being stored in the collecting section 8.

Then, at a time point when the pillar-shaped portion 2 has moved to the third position P3, the collecting section 8 and the collecting port 8a in the state of storing the medicinal solution 40 are exposed to the outside of the introduction port 31.

The user can test whether or not the medicinal solution 40 has such a concentration that the medicinal solution 40 can show a predetermined processing capability, for example, by inserting a test paper for measuring the concentration of the medicinal solution 40 into the collecting section 8. Note that the test for the medicinal solution 40 may be executed by sucking the medicinal solution 40 in the collecting section 8 by a pipette or the like.

Then, by the user releasing a hand from the handle section 3 in the state in which the pillar-shaped portion 2 is positioned at the third position P3, the pillar-shaped portion 2 automatically moves to the first position P1 by its own weight.

As described above, the medicinal solution collecting tool 1 of the present embodiment can collect the medicinal solution 40 used for a test to the outside of the medicinal solution storing section 30 only by grasping the handle section 3 and performing an operation of withdrawing the pillar-shaped portion 2 out of the medicinal solution storing section 30. Further, after the medicinal solution 40 is collected, the medicinal solution collecting tool 1 returns to an initial position before performing the collecting operation only by releasing the hand from the handle section 3. Thus, according to the medicinal solution collecting tool 1 of the present embodiment, it is possible to collect the medicinal solution 40 stored in the medicinal solution storing section 30 by an easy operation.

Further, in the present embodiment, it is possible to collect the medicinal solution 40 only by withdrawing the pillar-shaped portion 2 out of the medicinal solution storing section 30, and it does not happen that the collecting section 8 storing the medicinal solution 40 inclines to an angle at which the medicinal solution 40 spills. Therefore, in the present embodiment, it does not happen that surroundings around the medicinal solution storing section 30 are soiled by the medicinal solution spilling and scattering, unlike the conventional method of transferring the medicinal solution from a stop-cock to a beaker.

Further, in the medicinal solution collecting tool 1 of the present embodiment, when the pillar-shaped portion 2 is located at the first position P1, the pillar-shaped portion 2 is in such an attitude that the medicinal solution 40 in the collecting section 8 falls outside, and the collecting section 8 and the collecting port 8a sink under the medicinal solution 40. Thereby, all the medicinal solution 40 in the collecting section 8 is replaced with the medicinal solution 40 in the medicinal solution storing section 30 each time the pillar-shaped portion 2 goes and comes back between the first position P1 and the third position P3. Therefore, for example, it does not happen that the medicinal solution 40 with a certain concentration continues to stay in the collecting section 8. Therefore, according to the medicinal solution collecting tool 1 of the present embodiment, it is possible to collect the medicinal solution 40 equal to a latest state of the medicinal solution 40 in the medicinal solution storing section 30 for a test, and test the processing capability of the medicinal solution 40 accurately.

Figure 13:
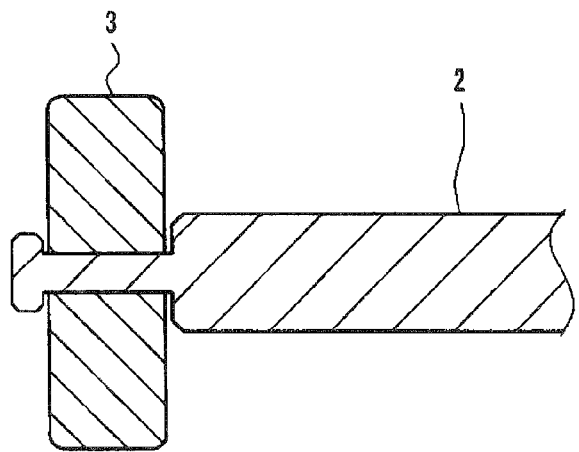
FIG. 13 is a partial cross-sectional view showing a first modification of the medicinal solution collecting tool of the first embodiment.

Note that, though the handle section 3 and the pillar-shaped portion 2 are fixed in the present embodiment described above, the handle section 3 may be rotatable around the axis relative to the pillar-shaped portion 2 as shown in FIG. 13 as a first modification.

In the embodiment described above, the handle section 3 also rotates together with the pillar-shaped portion 2 when the pillar-shaped portion 2 is caused to move in the axial direction between the first position P1 and the second position P2. In the present modification shown in FIG. 13, however, the handle section 3 does not rotate, and only the pillar-shaped portion 2 rotates. Therefore, in the present modification, it becomes unnecessary to twist the hand grasping the handle section 3 or change how to hold the handle section 3 at the time of withdrawing the medicinal solution collecting tool 1 out of the medicinal solution storing section 30, and the operation becomes easier.

Figure 14:
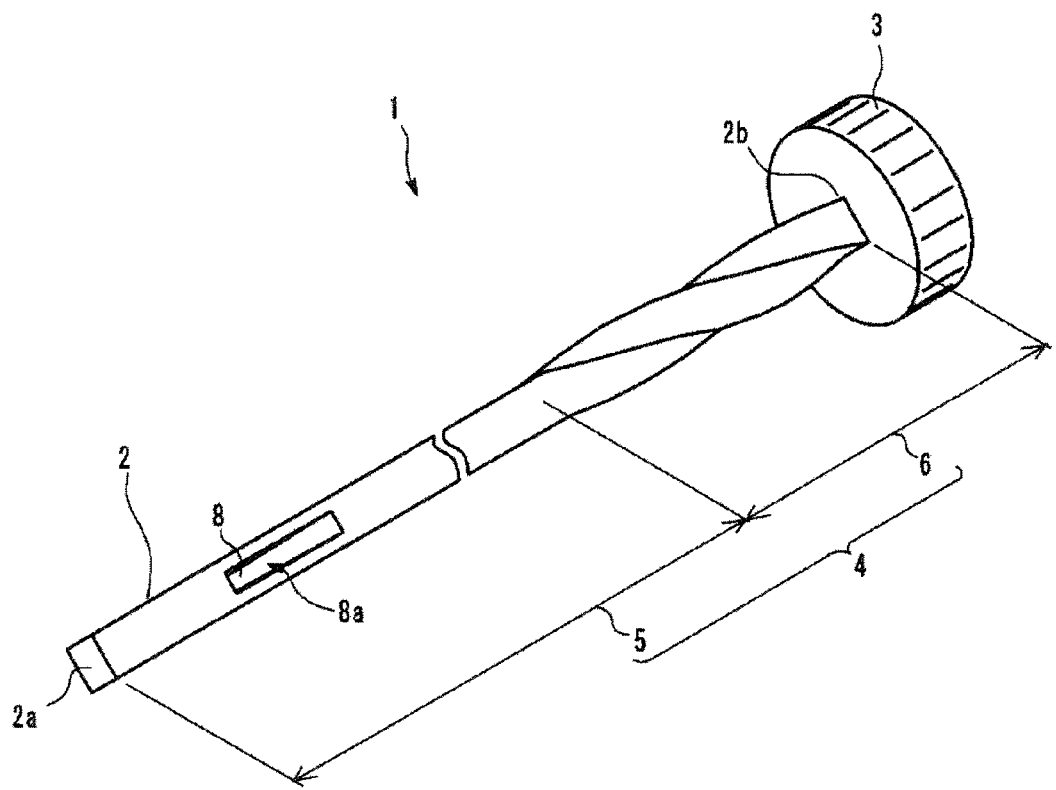
FIG. 14 is a partial cross-sectional view showing a second modification of the medicinal solution collecting tool of the first embodiment.

Further, though the guide section 4 is in a groove shape in the embodiment described above, the form of the guide section 4 is not limited to the groove shape. For example, if a cross-sectional shape of the pillar-shaped portion 2 is a rectangle as shown in FIG. 14 as a second modification, the guide section 4 can be an outer surface of the rectangular pillar-shaped portion 2. In the present modification, the follower 10 is constituted by a rectangular hole portion which slides in the axial direction along the outer surface of the rectangular pillar-shaped portion 2.

In the present modification, the guide section 4 includes the first guide section 5 formed by a prism-shaped outer surface, and the second guide section 6 provided on the withdrawal end side of the first guide section 5 and formed by an outer surface in a shape obtained by twisting a prism by an angle α.

(Second Embodiment)

Next, a second embodiment of the present invention will be described. Only differences from the first embodiment will be described below. Components similar to those of the first embodiment will be given same reference numerals, and description thereof will be appropriately omitted.

Figure 15:
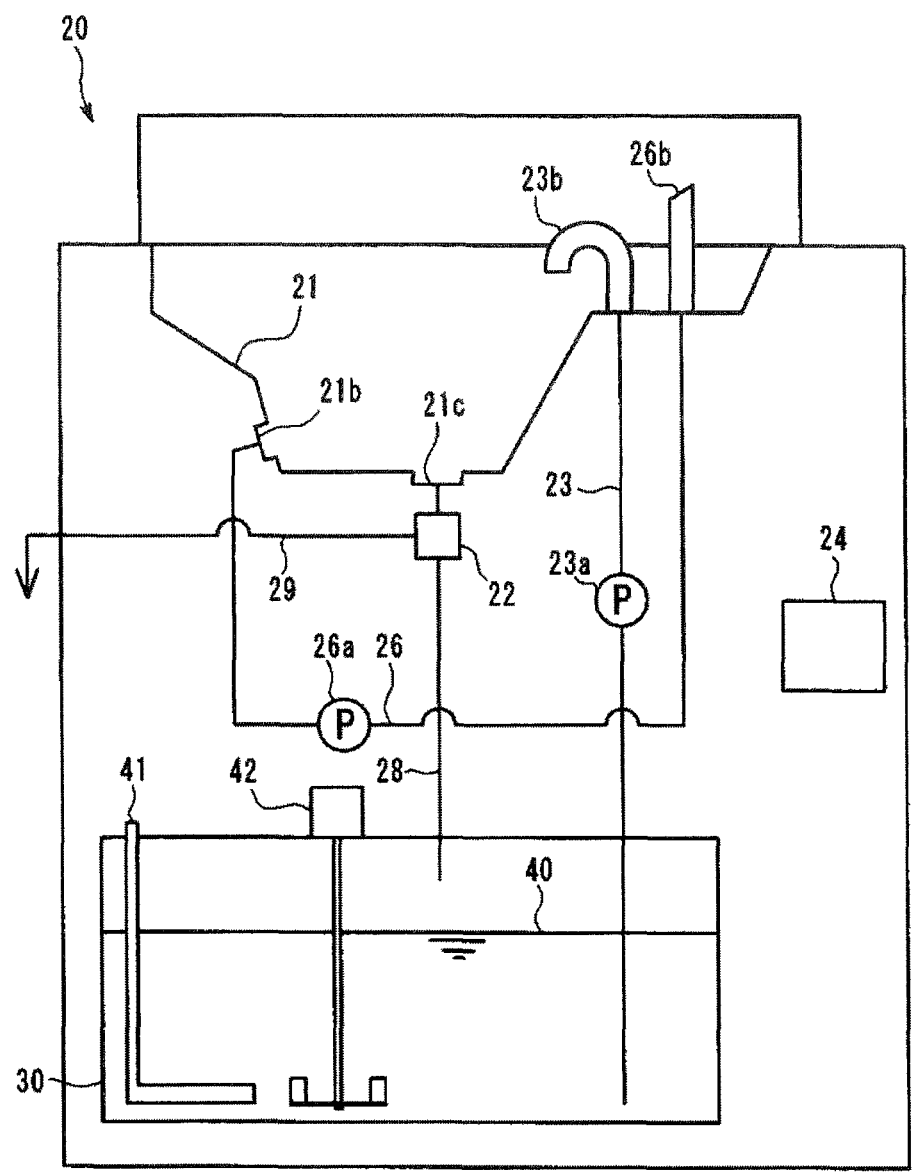
FIG. 15 is a diagram showing a schematic configuration of an endoscope cleaning/disinfecting apparatus of a second embodiment.

As shown in FIG. 15, an endoscope cleaning/disinfecting apparatus 20 of the present embodiment is provided with a heater 41 and a stirring device 42 in the medicinal solution storing section 30. The heater 41 is a device for heating the medicinal solution 40 stored in the medicinal solution storing section 30.

The stirring device 42 is a device which stirs the medicinal solution 40 stored in the medicinal solution storing section 30 to uniform temperature of the medicinal solution 40 in the medicinal solution storing section 30.

Figure 16:
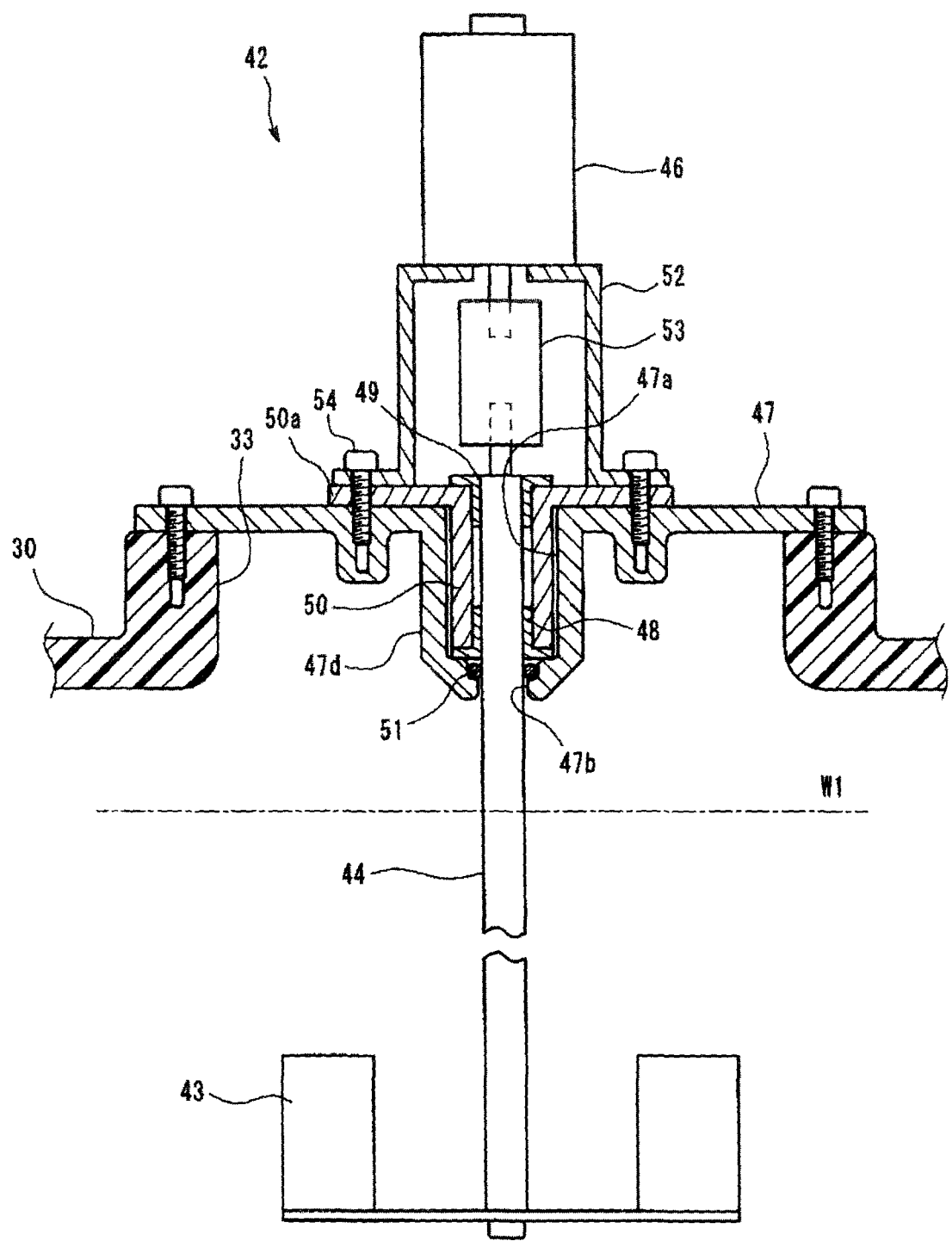
FIG. 16 is a cross-sectional view of a stirring device of the second embodiment.

As shown in FIG. 16, the stirring device 42 is provided with a motor 46, a shaft 44 which is rotation-driven by the motor 46, and a rotation fin 43 attached at a distal end portion of the shaft 44. The stirring device 42 stirs the medicinal solution 40 by causing the rotation fin 43 to rotate in the medicinal solution 40.

The stirring device 42 is inserted in an inside of the medicinal solution storing section 30 from a through hole 33 formed upper than the highest water level W1 of the medicinal solution storing section 30. The motor 46 and the shaft 44 are supported by a base portion 47 fixed on the medicinal solution storing section 30 in a manner that the base portion 47 seals the through hole 33. By removing the base portion 47 from the medicinal solution storing section 30, the whole stirring device 42 can be separated from the medicinal solution storing section 30.

A recessed portion 47a in a recess shape is formed from the outside to the inside of the medicinal solution storing section 30. The recessed portion 47a is provided in a protruding portion 47d projecting from the base portion 47 into the medicinal solution storing section 30. A through hole 47b through which the shaft 44 passes is provided on a bottom portion of the recessed portion 47a. A sealing member 51 is arranged between the through hole 47b and the shaft 44 to prevent vapor of the medicinal solution 40 from passing through the through hole 47b and leaking to the outside of the medicinal solution storing section 30.

Axial-direction positioning of the sealing member 51 is performed by the sealing member 51 being sandwiched between a first bearing 48 arranged in the recessed portion 47a, which is to be described later, and the bottom portion of the recessed portion 47a. Since the sealing member 51 is arranged upper than the highest water level W1 of the medicinal solution storing section 30, the sealing member 51 does not touch the medicinal solution 40, and deterioration of the sealing member 51 due to contact with the medicinal solution 40 can be prevented.

The shaft 44 is supported rotatably around the axis relative to the base portion 47, by the first bearing 48 and a second bearing 49 provided at positions separated from each other in the axial direction. The first bearing 48 and the second bearing 49 are fitted insides both ends of a cylinder-shaped bearing holding section 50 fixed in a state of being inserted in the recessed portion 47a, respectively. The bearing holding section 50 has a flange portion 50a projecting from the recessed portion 47a. The bearing holding section 50 is connected to the base portion 47 by a screw 54 piercing through the flange portion 50a.

By supporting the shaft 44 by the first bearing 48 and the second bearing 49 arranged separately from each other in the axial direction as in the present embodiment, it is possible to suppress shake movement of the shaft 44 and the rotation fin 43 caused in a case of rotation-driving the shaft 44. By suppressing the shake movement of the shaft 44 and the rotation fin 43, it is possible to arrange the shaft 44 and the rotation fin 43 near an internal wall surface of the medicinal solution storing section 30 and other members provided in the medicinal solution storing section 30 such as the heater 41 and reduce a size of the medicinal solution storing section 30.

The motor 46 is fixed on the base portion 47 via a motor holding section 52. In the present embodiment, the motor holding section 52 is connected to the base portion 47 together with the bearing holding section 50 by the same screw 54. A rotation axis of the motor 46 is coupled with a proximal end of the shaft 44 via a coupling 53.

Figure 17:
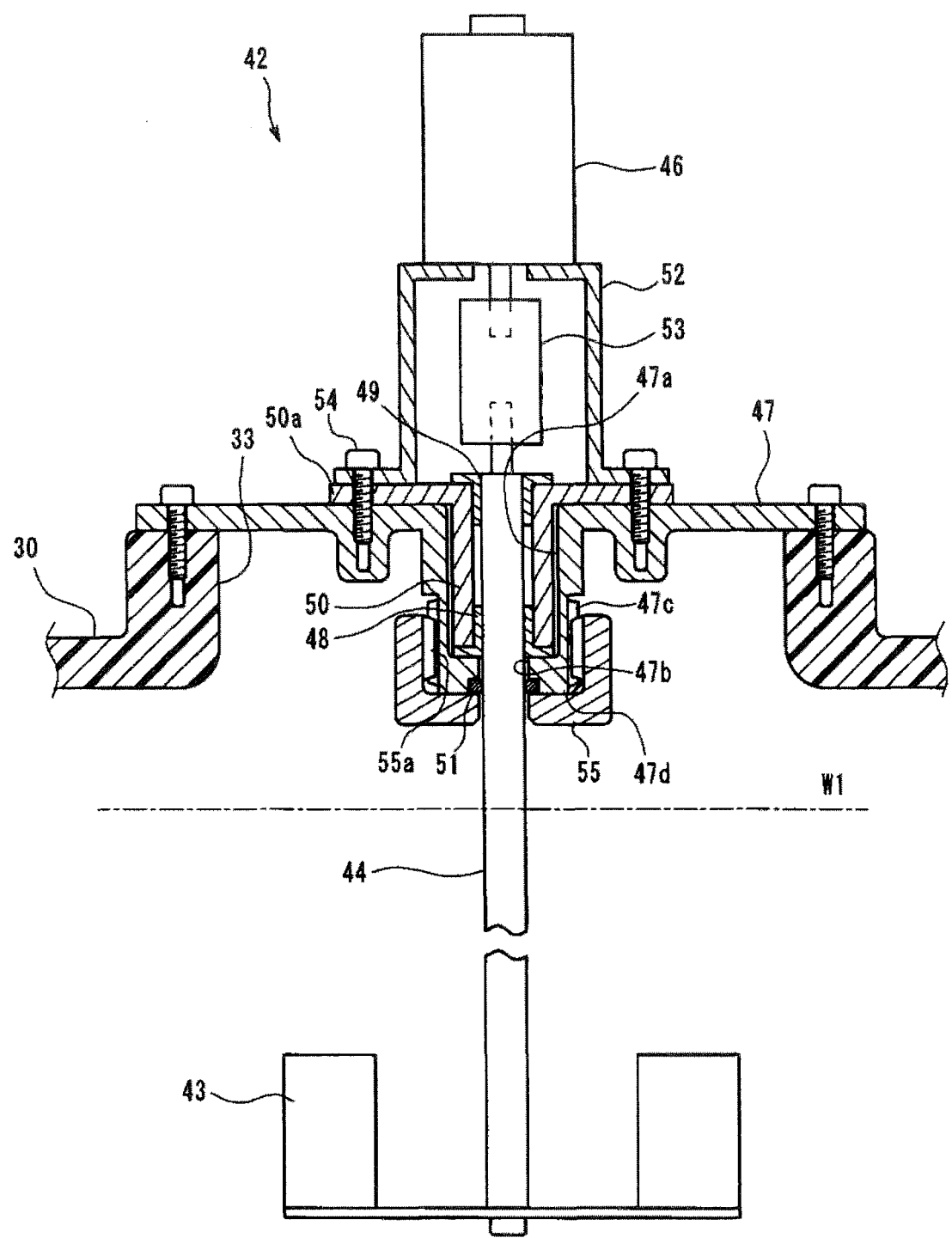
FIG. 17 is a cross-sectional view of the stirring device of a modification of the second embodiment.

FIG. 17 shows a modification of the present embodiment. In the present modification, axial-direction positioning of the sealing member 51 is performed by the sealing member 51 being sandwiched between a distal end portion of the protruding portion 47d of the base portion 47 which projects into the medicinal solution storing section 30 and a sealing member holding section 55.

A male screw portion 47c is formed at the distal end portion of the protruding portion 47d. The sealing member holding section 55 has a female screw portion 55a to engage with the male screw portion 47c. The sealing member holding section 55 is fixed on the base portion 47 by the female screw portion 55a engaging with the male screw portion 47c.

In the present modification, since it is possible to remove the sealing member 51 by removing the sealing member holding section 55 from the base portion 47, work of replacing the sealing member 51 becomes easy.

(Third Embodiment)

Next, a third embodiment of the present invention will be described. Only differences from the second embodiment will be described below. Components similar to those of the second embodiment will be given same reference numerals, and description thereof will be appropriately omitted.

Figure 18:
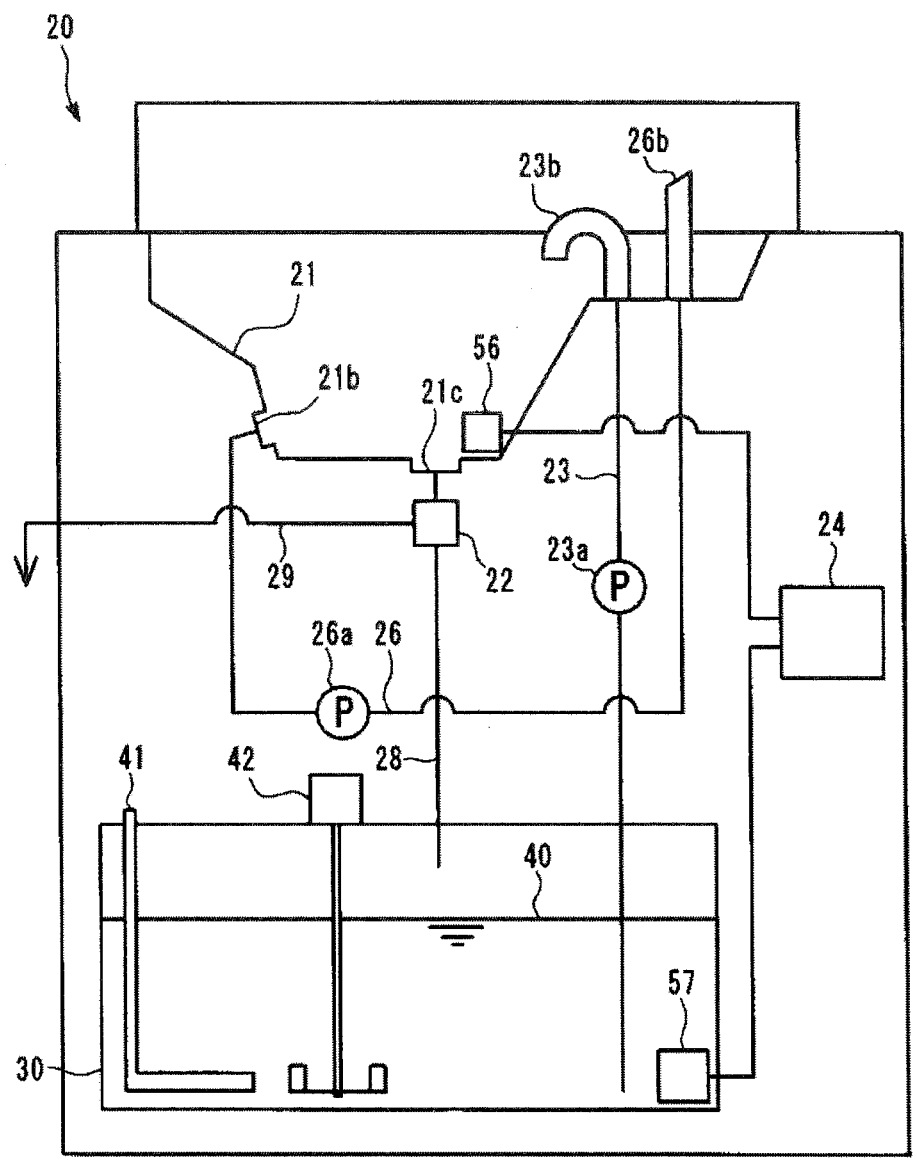
FIG. 18 is a diagram showing a schematic configuration of an endoscope cleaning/disinfecting apparatus of a third embodiment.

As shown in FIG. 18, an endoscope cleaning/disinfecting apparatus 20 of the present embodiment is provided with a first temperature sensor section 56 and a second temperature sensor section 57. The first temperature sensor section 56 is a device for measuring a temperature T1 of the liquid stored in the processing tank 21. Further, the second temperature sensor section 57 is a device for measuring a temperature T2 of the medicinal solution 40 stored in the medicinal solution storing section 30.

At time of performing the disinfection process by the endoscope cleaning/disinfecting apparatus 20, the medicinal solution injection pump 23a is caused to operate to transfer the medicinal solution 40, which is disinfection liquid, into the processing tank 21, and the medicinal solution 40 is stored in the processing tank 21.

Appropriate temperature, which is a predetermined temperature range appropriate to show the processing capability of the disinfection process is specified for the medicinal solution 40. Therefore, when the endoscope cleaning/disinfecting apparatus 20 operates, the temperature T2 of the medicinal solution 40 in the medicinal solution storing section 30 is measured by the second temperature sensor section 57, and, if the temperature T2 of the medicinal solution 40 in the medicinal solution storing section 30 is below the appropriate temperature, the heater 41 is caused to operate to heat the medicinal solution 40 in the medicinal solution storing section 30 to the appropriate temperature or a target temperature Tt which exceeds the appropriate temperature.

A value of the target temperature Tt is variable as described later. Note that an upper limit of the target temperature Tt is set to a temperature lower than a temperature at which deterioration of the medicinal solution 40 is promoted. A lower limit of the target temperature Tt is a temperature equal to or higher than a lower limit value of the appropriate temperature set for the medicinal solution 40.

In the present embodiment, at a stage prior to transferring the medicinal solution 40 from the medicinal solution storing section 30 to the processing tank 21, the temperature T2 of the medicinal solution 40 in the medicinal solution storing section 30 is measured by the second temperature sensor section 57.

Next, after transferring the medicinal solution 40 from the medicinal solution storing section 30 to the processing tank 21 and storing the medicinal solution 40 in the processing tank 21, the temperature T1 of the medicinal solution 40 in the processing tank 21 is measured by the first temperature sensor section 56.

Then, the temperature T2 of the medicinal solution 40 in the medicinal solution storing section 30 measured immediately previously and the temperature T1 of the medicinal solution 40 in the processing tank 21 are compared to determine an amount of temperature change $\Delta T$. The amount of temperature change $\Delta T$ is determined by $\Delta T=T2-T1$. If the temperature of the medicinal solution 40 decreases by transferring the medicinal solution 40 from the medicinal solution storing section 30 to the processing tank 21, the amount of temperature change ΔT takes a positive value.

In the present embodiment, after the amount of temperature change ΔT is calculated, ΔT is added to the value of the target temperature Tt. That is, temperature change in the medicinal solution 40 caused by transferring the medicinal solution 40 from the medicinal solution storing section 30 to the processing tank 21 is fed back to the target temperature Tt.

For example, when an atmospheric temperature and a water temperature are low in winter or the like, a wall surface temperature of the processing tank 21 is significantly lower than the appropriate temperature of the medicinal solution 40, and there may be a case where the temperature of the medicinal solution 40 significantly decreases by transferring the medicinal solution 40 from the medicinal solution storing section 30 to the processing tank 21. In the present embodiment, by adding the amount of temperature change ΔT measured immediately previously to the target temperature Tt, the temperature T2 of the medicinal solution 40 in the medicinal solution storing section 30 is increased by a temperature corresponding to decrease in the temperature of the medicinal solution 40 caused by transfer. Thereby, the disinfection process can be started without reheating the medicinal solution 40 in the processing tank 21.

(Fourth Embodiment)

Next, a fourth embodiment of the present invention will be described. Only differences from the first embodiment will be described below. Components similar to those of the first embodiment will be given same reference numerals, and description thereof will be appropriately omitted.

Figure 19:
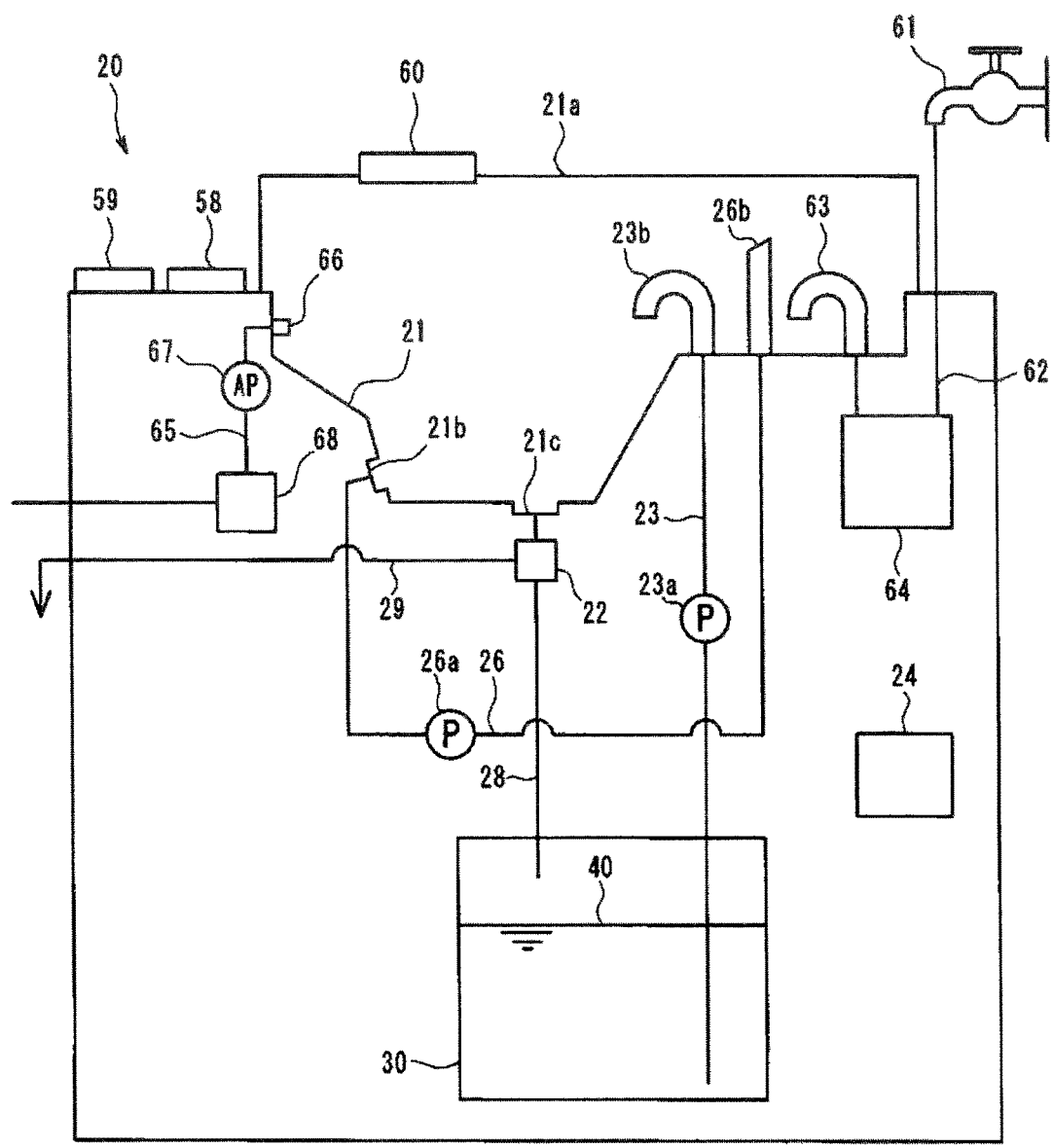
FIG. 19 is a diagram showing a schematic configuration of an endoscope cleaning/disinfecting apparatus of a fourth embodiment.

As shown in FIG. 19, an endoscope cleaning/disinfecting apparatus 20 is provided with an image display device 58 and an input device 59. The image display device 58 is a device which outputs information to the user by characters and images. The input device 59 is constituted, for example, by a touch panel and push button switches, and it is a device for inputting information from the user to the control section 24.

Further, the endoscope cleaning/disinfecting apparatus 20 is provided with a gas filter 60, a water filter 64, an air filter 68 and the like, which are parts requiring periodic replacement. The gas filter 60 is provided on a cover member 21a which seals the processing tank 21. The gas filter 60 is provided in a ventilation section inside and outside the processing tank 21, for example, to remove vapor of the medicinal solution 40.

The water filter 64 is provided in a water introduction conduit 62 for taking in tap water into the endoscope cleaning/disinfecting apparatus 20. One end of the water introduction conduit 62 is connected to a faucet 61, and the other end is connected to a water injection nozzle 63 provided in the processing tank 21. The water filter 64 filters tap water.

The air filter 68 is provided in an air introduction conduit 65 for sending air into the processing tank 21. One end of the air introduction conduit 65 is left open in atmosphere, and the other end is connected to a conduit connecting portion 66 provided in the processing tank 21. The conduit connecting portion 66 is connected to a conduit an endoscope is provided with, via a relay tube not shown. An air pump 67 is arranged on the air introduction conduit 65. By causing the air pump 67 to operate, air can be sent into the conduit of the endoscope. The air filter 68 filters the air to be sent into the conduit of the endoscope.

The endoscope cleaning/disinfecting apparatus 20 of the present embodiment makes it possible to input a date and time when periodic replacement parts such as the gas filter 60, the water filter 64, the air filter 68 and the like, are replaced via the input device 59 and cause a storage section to store the date and time of replacement. Further, the storage section stores available time periods of the periodic replacement parts. The available time period is a time period until replacement is required after use of a new periodic replacement part is started.

The control section 24 compares a stored last replacement date and time of a periodic replacement part with a current date and time to calculate an elapsed time period after the periodic replacement part was replaced. Then, if the elapsed time period is close to the available time period of the periodic replacement part or if the elapsed time period exceeds the available time period of the periodic replacement part, the control section 24 displays a warning on the image display device 58. Here, the warning displayed on the image display device 58 includes content for urging the user to replace the periodic replacement part. According to the present embodiment, it is possible to prevent failure to replace a periodic replacement part.

Note that the present invention is not limited to the embodiments described above but can be appropriately changed within a range not departing from the spirit or idea of the invention which can be read from the claims and the whole specification, and a medicinal solution collecting tool and an endoscope cleaning/disinfecting apparatus accompanied by such a change are also included in the technical scope of the present invention.

What is claimed is:

1. A medicinal solution collecting tool to be inserted into an introduction port of a medical solution storing section for endoscope reprocessing to collect a medicinal solution from an inside of the medicinal solution storing section, the medicinal solution collecting tool comprising:

a pillar-shaped portion comprising an insertion end and a withdrawal end, the pillar-shaped portion being configured to be inserted into the introduction port and movable in an axial direction in the introduction port;

a collecting section provided on the insertion end side of the pillar-shaped portion, the collecting section being a cavity for collecting the medicinal solution;

a collecting port which is an opening provided on a surface of the pillar-shaped portion, the collecting port communicating with the collecting section; and a guide section provided on the surface of the pillar-shaped portion, the guide section being configured to engage with the medical solution storing section and restrict the pillar-shaped portion inserted into the introduction port from rotating around an axis of the pillar shaped portion;

wherein the guide section comprises:

a first guide section that is convex or concave and parallel to an axial direction of the pillar-shaped portion, the first guide section being configured to engage with the medical solution storing section and restrict the pillar-shaped portion from rotating around the axis of the pillar-shaped portion such that the collecting port opens upward in a state where the pillar-shaped portion is inserted in the introduction port by a section from the insertion end to a position at a predetermined length toward the withdrawal end; and a second guide section provided on the withdrawal end side relative to the first guide section on the surface of the pillar-shaped portion, the second guide section being convex or concave and crossing the axial direction of the pillar-shaped portion, the second guide section being configured to engage with the medical solution storing section and cause the pillar-shaped portion to rotate around the axis of the pillar-shaped portion such that the collecting port is oriented downward as the pillar-shaped portion moves from the position toward the insertion end side in the axial direction in a state where a section of the pillar-shaped portion on the withdrawal end side relative to the position is inserted into the introduction port.

2. The medicinal solution collecting tool according to claim 1, wherein the first guide section and the second guide section are concave.

3. The medicinal solution collecting tool according to claim 1, wherein at least a part of the pillar-shaped portion where the first guide section and the second guide section are formed is cylinder-shaped.

4. An endoscope cleaning/disinfecting apparatus comprising:
   the medicinal solution collecting tool according to claim 1; and
   a medicinal solution storing section storing the medicinal solution, the medicinal solution storing section comprising an introduction port for introducing the medicinal solution collecting tool.

* * * * *